United States Patent [19]

Meul

[11] Patent Number: 4,843,166

[45] Date of Patent: Jun. 27, 1989

[54] 4-BENZYLOXY-3-PYRROLIN-2-ON-1-YL ACETAMIDE PRODUCTION

[75] Inventor: Thomas Meul, Visp, Switzerland

[73] Assignee: Lonza Ltd., Gampel/Valais, Switzerland

[21] Appl. No.: 181,646

[22] Filed: Apr. 14, 1988

Related U.S. Application Data

[62] Division of Ser. No. 60,262, Jun. 10, 1987.

[30] Foreign Application Priority Data

Jun. 26, 1986 [CH] Switzerland ..................... 2567/86

[51] Int. Cl.$^4$ ........................................... C07D 207/38
[52] U.S. Cl. ..................................................... 548/544
[58] Field of Search ........................................ 548/544

[56] References Cited

U.S. PATENT DOCUMENTS

| | | | |
|---|---|---|---|
| 2,535,010 | 12/1950 | Croxall et al. | 260/484 |
| 2,784,191 | 3/1957 | Fischer et al. | 260/294.7 |
| 4,118,396 | 10/1978 | Pifferi et al. | 260/326 |
| 4,124,594 | 11/1978 | Monguzzi et al. | 260/326.43 |
| 4,173,569 | 11/1979 | Banfi et al. | 260/326.43 |

FOREIGN PATENT DOCUMENTS 0192255 2/1986 European Pat. Off.
850007 7/1952 Fed. Rep. of Germany.
183756 11/1982 Japan.

OTHER PUBLICATIONS

MacKenzie et al., J.O.C.S., 20 No. 12, (1955), pp. 1695 and 1696.
G. Pifferi and M. Pinza, Il Farmaco, Ed. Sc., 1977, vol. 32, p. 602.
Koehler, Dissertation Bayreuth, (1985).
Sidgwick, "The Organic Chemistry of Nitrogen", 3rd Ed., Oxford (1966), p. 637.
Ho et al., "Cleavage of Ester and Ether with Iodotrimethylsilane", Angewandte Chemie, vol. 15, No. 12, (12/76), pp. 774 and 775.
Cram et al., J. Am. Chem. Soc., 1963, 85, pp. 1430–1437.
Chemical Abstracts 105:226341.
Chemical Abstracts vol. 52, 11124g.
Lowe, J. Chem. Soc., Perkin Trans. I, 1973, 2907–2910.

*Primary Examiner*—David B. Springer
*Attorney, Agent, or Firm*—Fisher, Christen & Sabol

[57] ABSTRACT

4-Benzyloxy-3-pyrrolin-2-on-1-yl acetamide is an advantageous intermediate product for the production of pharmaceutically effective 4-hydroxypyrrolidin-2-1-yl acetamide. Processes for the production of the intermediate product as well as the active substance are described.

11 Claims, No Drawings

4-BENZYLOXY-3-PYRROLIN-2-ON-1-YL ACETAMIDE PRODUCTION

This is a divisional of Application Ser. No. 060,262, filed on June 10, 1987.

BACKGROUND OF THE INVENTION

1. Field Of The Invention

The new 4-benzyloxy-3-pyrrolin-2-on-1-yl acetamide is a valuable intermediate product for the synthesis of cerebrally effective 4-hydroxypyrrolidin-2-on-1-yl acetamide (oxiracetam).

2. Background Art

A process is known from Pifferi et al., Il Farmaco, Ed. Sc., 1977, 32, 602, for producing the active substance. But a poor yield and expensive initial products make the process unprofitable.

BROAD DESCRIPTION OF THE INVENTION

The main object of the invention is to provide a production process which does not have such disadvantages.

This object was able to be attained in a remarkably simple way by the discovery of the new intermediate 4-benzyloxy-3-pyrrolin-2-on-1-yl acetamide. This intermediate material can be reached either from a 4-($C_1$-$C_2$)-alkoxy-3-pyrrolin-2-one or a 4-($C_1$-$C_2$)-alkoxy-3-pyrrolin-2-on-1-yl acetic acid-($C_1$-$C_4$) alkyl ester. More specifically, 4-benzyloxy-3-pyrrolin-2-on-1-yl acetamide of the formula:

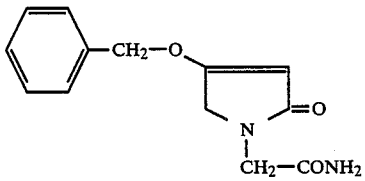

is produced by either transesterification of a 4-($C_1$-$C_2$)-alkoxy-3-pyrrolin-2-one with benzyl alcohol in the presence of an acid to 4-benzyloxy-3-pyrrolin-2-one, alkylation with 2-bromoacetic acid-($C_1$-$C_4$) alkyl ester in the presence of an alkali hyride to 4-benzyloxy-3-pyrrolin-2-on-1-yl acetic acid ($C_1$-$C_4$) alkyl ester and finally conversion with ammonia to the end product, or conversion of a 4-($C_1$-$C_2$) alkoxy-3-pyrrolin-2-on-1-yl acetic acid ($C_1$-$C_4$) alkyl ester with benzyl alcohol in the presence of an acid to 4-benzyloxy-3-pyrrolin-2-on-1-yl acetic acid benzyl ester and, optionally without its isolation, with ammonia to the end product.

Initial products with longer alkoxy or alkyl groups can easily be used. But since these groups are again split off in the course of the process, such compounds are of no significant interest.

Starting from 4-($C_1$-$C_2$)-alkoxy-3-pyrrolin2-one conversion to 4-benzyloxy-3-pyrroline-2-one is performed in a first step in the presence of an acid with benzyl alcohol. As acids for this step, sulfonic acids, such as, methane sulfonic acid or p-toluene sulfonic acid, are suitably used in catalytic amounts of suitably 0.05 to 0.2 mol. It is advantageous to operate directly in benzyl alcohol as the solvent. Benzyl alcohol is suitably used in an amount of 1.5 to 5 mol per mol of initial product.

The reaction temperature is advantageously in the range of 60° to 100° C. Since in this reaction a transesterification is involved, it is advantageous to perform the reaction at reduced pressure between 10 and 50 mbars to remove from the equilibrium the low-boiling alcohols that have split off.

After the completed reaction, i.e., after about 10 to 25 hours (depending on the catalyst amount of sulfonic acid), the 4-benzyloxy-3-pyrrolin-2-one can be worked up in a usual way, e.g., by azeotropic separation of the excess benzyl alcohol and optionally by crystallization of the resulting product.

In a second step the resultant product is converted with a bromoacetic acid ($C_1$-$C_4$) alkyl ester in the presence of an alkali hydride to 4-benzyloxy3-pyrrolin-2-on-1-yl acetic acid-($C_1$-$C_4$) alkyl ester. Bromoacetic acid ethyl ester in an amount of suitably 1 to 1.5 mol per mol of 4-benzyloxy-3-pyrrolin-2-one is used as the preferred bromoacetic acid alkyl ester. Sodium hydride is used as the preferred alkali hydride in an amount of 1 to 1.5 mol per mol of the 4-benzyloxy-3-pyrrolin-2-one.

Advantageously, the operation is performed in a polar, aprotic solvent, such as dimethylformamide, dimethyl acetamide and acetonitrile, (especially advantageously in acetonitrile as the solvent, at a reaction temperature of 0° to 40° C.

The resultant 4-benzyloxy-3-pyrrolin-2-on-1-yl acetic acid-($C_1$-$C_4$) alkyl ester can be converted in a last stage with ammonia to 4-benzyloxy-3-pyrrolin-2-on-1-yl acetamide. Suitably in this case the procedure is such that the initial product is advantageously dissolved in an alcohol, such as methanol or ethanol, the alcohol being previously saturated with gaseous ammonia at −10° to 0° C., and then the reaction mixture is stirred in an autoclave at 60° to 80° C. for 10 to 15 hours.

After the usual work-up, the desired intermediate product can be obtained in good yield and quality.

If the start is made from 4-($C_1$-$C_4$)-alkoxy-3-pyrrolin-2-on-1-yl acetic acid ($C_1$-$C_4$) alkyl ester, a conversion is performed in a first step with benzyl alcohol, in an acid manner to 4-benzyloxy-3-pyrrolin-2-on-1-yl acetic acid benzyl ester. As acids for this step, suitably sulfonic acids, preferably methane sulfonic acid or p-toluene sulfonic acid, in catalytic amounts of suitably 0.05 to 0.2 mol are used.

It is advantageous to work directly in benzyl alcohol as the solvent. The benzyl alcohol is suitably used in an amount of 2.5 to 5.0 mol per mole of initial product. The reaction temperature is advantageously in the range of 80° to 120° C. As in the production of 4-benzyloxy-3-pyrrolin-2-one, it is advantageous to perform the reaction at reduced pressure, preferably between 10 to 50 mbars.

After reaction is completed, i.e., after about 7 to 10 hours, 4-benzyloxy-3-pyrrolin-2-on-1-yl acetic acid benzyl ester can be obtained after the usual work-up and optionally by purification by means of recrystallization.

In a last step, conversion with ammonia to the desired intermediate product to 4-benzyloxy-3-pyrrolin-2-on-1-yl acetamide can then be performed. Advantageously the alcohol, preferably methanol and ethanol, functioning as solvent for this purpose is saturated with gaseous ammonia at -10° to 0° C., then the 4-benzyloxy-3-pyrrolin-2-on-1-yl acetic acid benzyl ester is added and finally the reaction mixture is stirred in the autoclave at 60° to 80° C. for 6 to 10 hours.

After a simple work-up, the desired intermediate product can be obtained in good yield and quality.

The 4-benzyloxy-3-pyrrolin-2-on-1-yl acetamide can be used as an especially advantageous intermediate product for production of cerebrally effective 4-hydroxypyrrolidin-2-on-1-yl acetamide.

Suitably for this purpose catalytic hydrogenation is performed in a first step.

Noble metal catalysts are suitably used as catalysts, which causes a selective debenzylation. Preferably palladium, applied to a usual support material, preferably on activated carbon, with a catalyst content of 1 to 10 percent is used. The catalyst amount suitably ranges between 5 and 10 percent by weight, in relation to the amount of 4-benzyloxy-3-pyrrolin-2-on-1-yl acetamide used.

The intermediately resultant 2,4-dioxopyrrolidin-1-yl acetamide can be reduced with complex borohydrides, preferably with alkali borohydrides, especially preferably with sodium borohydride, to the end product. Thus, it is advantageous to perform the debenzylation in a polar aprotic solution, such as, dimethylformamide or dimethyl acetamide, under a pressure of suitably 1 to 20 bars and at a temperature suitably between 0° and 30° C. The alkali borohydride is preferably used in an amount of 0.5 to 0.8 mol per mol of 4-benzyloxy-3-pyrrolin-2-on-1-yl acetamide.

While maintaining the polar aprotic solvent, the operation is suitably performed at a temperature of 0° to 30° C. In this way, a corresponding advantage of the process described here applies, because the sensitive 2,4-dioxopyrrolidin-1-yl acetamide tending to dimerization is kept in solution and must not be isolated, whichever, is possible.

If catalytic hydrogenation is selected for conversion of the intermediate 2,4-dioxopyrrolidin-1-yl acetamide to the end product, advantageously the operation for the catalytic hydrogenolysis is performed in a polar protic anhydrous solvent, such as, methanol, ethanol or acetic acid, at suitably 1 to 20 bars and a temperature of suitably 0° to 30° C. The catalyst and catalyst amount advantageously remain unchanged with respect to the catalytic hydrogenolysis in polar aprotic solvents.

The catalytic hydrogenation is then suitably performed with platinum catalysts, such as platinum oxide or platinum, applied in an amount of 1 to 10 percent to a support, preferably to activated carbon.

The catalyst amount suitably ranges between 1 and 10 percent by weight in relation to the 4-benzyloxy-3-pyrrolin-2-on-1-yl acetamide. The hydrogen pressure suitably is between 5 to 20 bars, the temperature is between 0° and 30° C. Also in this catalytic reduction it is advantageous to keep the intermediately formed 2,4-dioxopyrrolidin-1-yl acetamide in solution and not to isolate it.

It is especially preferable to perform the debenzylation of the 4-benzyloxy-3-pyrrolin-2-on-1-yl acetamide by catalytic hydrogenolysis and the catalytic reduction by hydrogenation of the intermediate 2,4-dioxopyrrolidin-1-yl acetamide with hydrogen as a one-pot process with palladium/platinum mixed catalysts. Again the polar aprotic anhydrous solvents, such as, methanol, ethanol or anhydrous acetic acid, are suitably used. The hydrogen pressure ranges advantageously between 5 and 20 bars and the temperature between 0° and 30° C. Suitably a palladium/platinum mixed catalyst is used, whose palladium to platinum ratio is 5 to 1 to 1 to 2. The palladium portion is preferably used in an amount of 1 to 10 percent, applied to a usual support, preferably to activated carbon. The platinum portion can be present as platinum oxide or also as platinum, applied in an amount of 1 to 10 percent to a usual support, preferably to activated carbon. The mixed catalyst is used in an amount of suitably 5 to 15 percent by weight, in relation to the 4-benzyloxy-3-pyrrolin-2-on-1-yl acetamide.

The work-up of the end product, independently of which process is selected, can take place in a usual process manner. The resultant 4-hydroxypyrrolidin-2-on-1-yl acetamide can optionally be purified by recrystallization.

Via the new 4-benzyloxy-3-pyrrolin-2-on-1-yl acetamide as a new intermediate product and with the help of the process according to the invention, one can in the described way produce 4-hydroxy-3-pyrrolidin2-on-1-yl acetamide in good yields and in purities greater than 98 percent.

DETAILED DESCRIPTION OF THE INVENTION

EXAMPLE 1

(a) Production of 4-benzyloxy-3-pyrrolin-2-on-1-yl acetic acid benzyl ester 20.8 g of 4-methoxy-3-pyrrolin-2-1-yl acetic acid ethyl ester was dissolved in 44.1 g of benzyl alcohol, mixed with 1.0 g of methane sulfonic acid and stirred at 80° C. and 20 mbars for 12 hours. Then the reaction solution was mixed with 250 ml of methylene chloride and 500 ml of ice water, and neutralized with 10 ml of saturated $NaHCO_3$ solution. After drying of the organic phase over $Na_2SO_4$ and evaporation of the solvent, the residue was mixed with 400 ml of a 2:1 mixture of ice water and ethanol. As a result the product crystallized out. The yield was 25.8 g (76 percent). TLC showed no byproducts. The melting point of the product was 92° to 94° C. For the product:

NMR: (300 MHz, $CDCl_3$) δ in ppm, 7.45–7.29 (m, 10H), 5.20 (s, 1H), 5.16 (s, 2H), 4.98 (s, 2H), 4.22 (s, 2H), 4.03 (s, 2H).

MS: (70 eV): 337 ($M^+$, 2), 246 (7), 202 (14), 145 (10), 91 (100), 65 (12).

(b) Production of 4-benzyloxy-3-pyrrolin-2-on-1-yl acetamide 25.0 g of 4-benzyloxy-3-pyrrolin-2-on-1-yl acetic acid benzyl ester was dissolved in 500 ml of methanol and stirred at 40° C. with passing of gaseous $NH_3$ for 5 hours. Then the reaction solution was evaporated and the residue was mixed with 50 ml of acetone. The precipitated crystals were filtered by suction and dried. 15.2 g of TLC pure product with a melting point of 174.5 to 175.5° C. was obtained. For the product:

NMR: (300 MHz, $MDSO-d_6$) δ in ppm, 7.50–7.32 (m, 6H), 7.05 (br. s, 1H), 5.27 (s, 1H), 5.06 (s, 2H), 4.20 (s, 2H), 3.85 (s, 2H).

MS: (70 eV): 246 ($M+m$, 20), 229 (23), 202 (49), 145 (30), 91 (100), 65 (52).

EXAMPLE 2

(a) Direct production of 4-benzyloxy-3-pyrrolin-2-on-1-yl acetamide from 4-methoxy-3-pyrrolin-2-on-1-yl acetic acid methyl ester 25.0 g (0.132 mol) of 4-methoxy-3-pyrrolin-2-on-1-yl acetic acid methyl ester (98.0 percent), 41.7 g (0.38 mol) of benzyl alcohol and 1.9 g (19.8 mmol) of methane sulfonic acid were stirred for 8 hours at 110° C. in a water jet vacuum at 20 mbars. Then diluting with 167 ml of methylene chloride and mixing with 84 ml of ice water were performed. The aqueous phase was neutralized with 19.8 ml of saturated $NaHCO_3$ solution and extracted twice with 70 ml each of methylene chloride. The organic phases were combined, dried over Na₂SO₄ and concentrated in the rotary evaporator. The residue (57.7 g) was added to a methanol solution (34 ml) saturated with gaseous NH₃ at −10° C. and stirred in the autoclave at 70° to 80° C. for 9 hours. Then the methanol was evaporated, the residue mixed with 100 ml of carbon tetrachloride, cooled to 5° C. and the precipitated crystals were filtered by suction. The raw product (32.0 g) was recrystallized hot from 31 ml of water. 26.3 g of nearly white product with a content after HPLC of 97.9 percent was obtained. The yield was 79.4 percent.

EXAMPLE 3

(a) Production of 4-benzyloxy-3-pyrrolin-2-one 5.7 g of 4-methoxy-3-pyrrolin-2-one and 10.8 g of benzyl alcohol were mixed with 0.4 g of methane sulfonic acid and stirred for 24 hours at 80° C. and 20 mbars. Then the reaction solution was mixed with 50 ml of ice water and 100 ml of methylene chloride and neutralized with 4 ml of saturated NaHCO₃ solution. The aqueous phase was extracted twice more with 50 ml each of methylene chloride. After drying of the organic phase over Na₂SO₄ and distilling off of the solvent, the residue was mixed with 150 ml of ice water, heated to 100° C. and 100 ml of water-benzyl alcohol was azeotropically distilled off. The crystals precipitated during the cooling were recrystallized hot from 50 ml of toluene. 6.7 g of white, crystalline product with a melting point of 147° to 148° was obtained. For the product:

NMR: (300 MHz, DMSO=d₆), 7.38 (m, 5H), 6.20 (br. s, 1H), 5.16 (s, 1H), 4.98 (s, 2H), 3.98 (s, 2H).

MS: (70 eV): 189 (m+, 40), 172 (18), 132 (51), 91 (100).

(b) Production of 4-benzyloxy-3-pyrrolin-2-on-1-yl acetamide from 4-benzyloxy-3-pyrrolin-2-one 8.4 g of 4-benzyloxy-3-pyrrolin-2-one and 9.8g of bromoacetic acid ethyl ester (95 percent) were dissolved in 50 ml of anhydrous acetonitrile and cooled to 0° C. To this reaction solution was added within 20 minutes 1.67 g of sodium hydride (80 percent in white oil). Additional stirring for 2 hours was performed, acidification was performed with concentrated hydrochloric acid to pH 6 to 7 and the solvent was distilled off. The residue was taken up in water/methylene chloride. After separation of the organic phase, 14.4 g of raw product was obtained. This raw product was dissolved in 20 ml of methanol, which was previously saturated with gaseous ammonia at −10° to 0° C. The reaction solution was stirred in the autoclave for 12 hours at 60° to 80° C. After distilling off of the methanol and washing of the raw product with carbon tetrachloride, recrystallization from water was performed. 5.1 g of TLC pure product was obtained.

EXAMPLE 4

Catalytic hydrogenolysis and hydrogenation of 4-benzyloxy-3-pyrrolin-2-on-1-yl acetamide 3.00 g of 4-benzyloxy-3-pyrrolin-2-on-1-yl acetamide was dissolved in 30 ml of concentrated acetic acid and mixed with 240 mg of palladium 5 percent on activated carbon and 24 mg of platinum oxide. Hydrogenolysis and hydrogenation at 15 bars of hydrogen pressure and room temperature were performed for 65 hours. Then filtering off from the catalyst and evaporation of the solvent were performed. The residue was picked up in H₂O and allowed to run over 5.0 g of weakly basic ion exchanger. The water was distilled off and the residue mixed with 10 ml of acetone. 1.53 g of nearly white 4-hydroxypyrrolidin-2-on-1-yl acetamide with a melting point of 163.5° to 165.7° C. was obtained.

EXAMPLE 5

Hydrogenolysis and NaBH₄ reduction of 4-benzyloxy-3-pyrrolin-2-on-1-yl acetamide 10.0 g of 4-benzyloxy-3-pyrrolin-2-on-1-yl acetamide was hydrogenolyzed in 33 ml of dimethylformamide in the presence of 800 mg of palladium 5 percent on activated carbon at an H₂ pressure of 20 bars and at room temperature for 5 hours. Then the catalyst was filtered off and the filtrate was instilled within an hour at room temperature into a solution of 1.1 g of sodium boron hydride in 17 ml of dimethylformamide. Two additional hours of stirring was performed and the reaction solution was acidified with 3 ml of 1 to 1 mixture of formic acid and methanol. The solvents were distilled off. The residue was taken up in 100 ml of ice water, after that it was filtered over 80 g of strongly acidic ion exchanger and then over 80 g of weakly basic ion exchanger. The aqueous solution was evaporated and the residue taken up in 70 ml of methanol. 50 ml of methanol was distilled off, with the 4-hydroxypyrrolidin-2-1-yl acetamide precipitating as microcrystalline pecipitate. 4.2 g of product with a melting point of 166.2° to 167.3° C. (HPLC content 96.9 percent) was obtained.

Recrystallization from acetic acid/acetone in a ratio of 1 to 3 yielded a product with a melting point of 168° to 169.5° C. and an HPLC content of 99.0 percent.

What is claimed is:

1. Process for the production of 4-Benzyloxy-3-pyrrolin-2-on-1-yl acetamide of the formula:

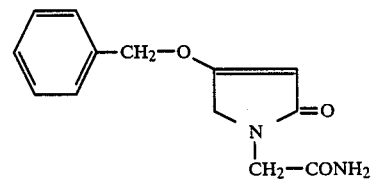

Comprising transetherifying a 4-(C₁–C₂)-alkoxy-3-pyrrolin-2-one with benzyl alcohol in the presence of an acid to 4-benzyloxy-3-pyrrolin-2-one, alkylating the transetherified compound with 2-bromoacetic acid-(C₁–C₄) alkyl ester in the presence of an alkali hydride to 4-benzyloxy-3-pyrrolin-2-on-1-yl acetic acid (C₁–C₄) alkyl ester, and converting the alkylated compound with ammonia to the end product.

2. Process according to claim 1 wherein a sulfonic acid is used as the acid for the transesterification of the 4-(C₁–C₂) alkoxy-3-pyrrolin-2-one.

3. Process according to claim 2 wherein the transesterification of the 4-(C₁–C₂) alkoxy-3pyrrolin-2-one is performed at a temperatures of 60° to 100° C. at a reduced pressure.

4. Process according to claim 1 wherein the reaction of the 4-benzyloxy-3-pyrrolin-2-on-1-yl acetic acid (C₁–C₄) alkyl ester with ammonia takes place at a temperature of 60° to 80° C. in an autoclave.

5. Process according to claim 1 wherein the transesterification of the 4-(C₁–C₂) alkoxy-3-pyrrolin-2-one is performed at a temperatures of 60° to 100° C. at a reduced pressure.

6. Process according to claim 1 wherein the 4-benzyloxy-3-pyrrolin-2-on-1-yl acetic acid (C₁–C₄) alkyl ester is fed, without isolation, to the reaction with ammonia.

7. Process according to claim 1 wherein the reaction of the 4-benzyloxy-3-pyrrolin-2-on-1-yl acetic acid ($C_1$–$C_4$) alkyl ester with ammonia takes place at a temperature of 60° to 80° C. in an autoclave.

8. Process according to claim 1 wherein a sulfonic acid is used as acid for the transesterification of the 4-($C_1$–$C_2$)-alkoxy-3-pyrrolin-2-on-1-yl acetic acid ($C_1$–$C_4$) alkyl ester.

9. Process according to claim 8 wherein the transesterification of the 4-($C_1$–$C_2$) 4-alkoxy-3-pyrrolin-2-on-1-yl acetic acid ($C_1$–$C_4$) alkyl ester is performed at a temperature of 80° to 120° C. under reduced pressure.

10. Process according to claim 1 wherein the transesterification of the 4-($C_1$–$C_2$) alkoxy-3-pyrrolin-2-on-1-yl acetic acid ($C_1$–$C_4$) alkyl ester is is performed at a temperatures of 80° to 120° C. under reduced pressure.

11. Process according to claim 1 wherein the reaction of the 4-benzyloxy-3-pyrrolin-2-on-1-yl acetic acid benzyl ester takes place, without its isolation, with ammonia at a temperature of 60° to 80° C. in an autoclave.

* * * * *